United States Patent [19]

Whalen

[11] Patent Number: 5,354,329
[45] Date of Patent: Oct. 11, 1994

[54] VASCULAR PROSTHESIS HAVING ENHANCED COMPATIBILITY AND COMPLIANCE CHARACTERISTICS

[75] Inventor: Robert L. Whalen, Cambridge, Mass.

[73] Assignee: Whalen Biomedical, Inc., Cambridge, Mass.

[21] Appl. No.: 114,607

[22] Filed: Aug. 31, 1993

Related U.S. Application Data

[63] Continuation of Ser. No. 869,944, Apr. 17, 1992, abandoned.

[51] Int. Cl.$^5$ .......................... A61F 2/06; A61F 2/02; A61F 2/04
[52] U.S. Cl. .......................... 623/1; 623/11; 623/12
[58] Field of Search .......................... 623/1, 11, 12, 66

[56] References Cited

U.S. PATENT DOCUMENTS

| | | | |
|---|---|---|---|
| 4,304,010 | 12/1981 | Mano | 3/1.4 |
| 4,321,711 | 3/1982 | Mano | 3/1.4 |
| 4,731,037 | 3/1988 | Robinson | 623/1 |
| 4,822,361 | 4/1989 | Okita et al. | 623/12 |
| 4,834,746 | 5/1989 | Kira | 623/1 |

OTHER PUBLICATIONS

G. Wilson, et al. *The Composite Corethane/Dacron Vascular Prosthesis: Canine In Vivo Evaluation of 4 mm Diameter Grafts with 1 Year Follow-Up*, Toronto General Hospital, University of Guelph and Corvita Corporation, 1992.

*Primary Examiner*—David Isabella
*Assistant Examiner*—Dinh X. Nguyen
*Attorney, Agent, or Firm*—Lorusso & Loud

[57] ABSTRACT

A method and apparatus for manufacturing a circulatory system non-pyrogenic vascular prosthesis comprising a multilaminar tubular member comprising an interior strata, a unitary medial strata and an exterior strata. The interior strata bears a pseudoneointima facilitating lumen surface and the exterior strata bears a stabilization promoter surface. The interior and exterior stratum being separated solely by said unitary medial strata which comprises an exclusionary boundary.

8 Claims, 5 Drawing Sheets

VASCULAR PROSTHESIS HAVING ENHANCED COMPATIBILITY AND COMPLIANCE CHARACTERISTICS

This is a continuation of copending application Ser. No. 07/869,944 filed on Apr. 17, 1992, now abandoned.

BACKGROUND OF THE INVENTION

1. Field of the Invention

This invention relates generally to a tubular prosthesis and is directed more particularly to a vascular prosthesis adapted to be compliance matched to a vessel or artery in which the prosthesis is implanted.

2. Description of the Prior Art

The development of small vessel prostheses for vascular surgery is known in the art. However, while conventional DACRON ® prostheses maintain long-term patency in large calibers, they are not usable in small sizes. The term DACRON ® is a Trademark for a polyester fiber made from polyethylene terephthalate. Moreover, alternative prostheses, such as those manufactured from various types of bioprosthetic as well expanded TEFLON (ePTFE) synthetic prostheses, which are now available for the reconstruction of smaller and more peripheral arteries such as the coronary and tibial vessels are also inadequate.

Bypasses to the popliteal and infrapopliteal vessels using bioprosthetic umbilical vein prostheses, for example, are complicated by decreased patency and deterioration of the biologic prostheses after three to five years. Similarly, while ePTFE prosthesis initially seemed quite promising experimentally when compared to conventional prostheses, its long term patency in small caliber grafts also has not been acceptable.

In addition, it has long been postulated that the response at the anastomoses of a synthetic prosthesis which has not been perfectly matched to the natural tissue of the host is an important factor in the poor performance of available small vessel prostheses. A vascular prosthesis which is designed to correspond to the exact dimensions and elasticity of the host is thought to lessen the potential for intimal hyperplasia at the anastomoses, an almost universal finding with conventional synthetic vascular prostheses. Intimal hyperplasia is especially compromising to the function of a small caliber prosthesis, since it narrows the already limited available lumen and more significantly alters flow patterns compared to a large caliber vessel.

Both DACRON and ePTFE prostheses have little radial compliance. It would seem reasonable to assume that the pulse pressure in the arterial circulation, which produces distension of the biologic vessels on each heartbeat, creates a boundary condition at the artery/prosthesis junction leading to relative motion between them and stress concentration. That is, the arterial tissue normally distends on each beat, but at the anastomotic site, it is constrained by the rigid prosthesis which does not correspond to the host. This chronic irritation and stress at the anastomoses may result in endothelial injury, smooth muscle cell proliferation, and intimal thickening.

While localized trauma to the host tissue is potentially involved in the development of fibrous intimal hyperplasis, it also has been shown recently that mismatch of the prosthesis with the host results in significantly different flow patterns at the anastomoses even in the absence of localized narrowing of the vessel. These flow disturbances may therefore similarly provide a mechanism responsible for the problems observed at the anastomoses with conventional small vessel prostheses. A further finding has shown that implanted compliant grafts have tended to significantly lose their compliance in vivo during healing.

Therefore, is is desirable for a small caliber prosthesis to retain its compliance properties following healing of the perigraft tissues. The prosthesis must retain its compliance properties in order to minimize its potential to produce intimal hyperplasia or elicit excessive pseudo-neointima derived from blood, represented hereinafter by the acronym, PNI, deposition secondary to disturbances of flow patterns at the anastomoses. It was further postulated that to achieve a prosthesis which remains stable with its host, it is important to control healing around the prosthesis so that the prosthesis' compliance properties will remain in a physiologic range.

In one embodiment of the present invention, the exterior textured surface provides for tissue attachment to the implant surface and a diminished foreign body response at the the tissue interface.

There are conventional DACRON prostheses which are textured on both their exterior and interior surfaces, but they do not have radial compliance. DACRON prostheses with an external velour surface were actually tried many years ago, but the function of the external velour was simply to promote more vigorous perigraft tissue in growth through the prosthesis wall to better anchor the PNI.

Replamineform process prostheses are perhaps the most similar textured surface prosthesis to the prosthesis of the present invention, though the prosthesis wall of those prostheses is porous. Made using calcite sea urchin spines as a form for molding a porous elastomeric tube, replamineform prostheses have both porosity and remain stable with their host. Those prostheses are certainly not readily manufacturable, however, nor is their stability with the host easily controlled. Because the wall is uniformly porous, stability with the host can be varied feasibly only over a limited range, and do not remain so when implanted.

Additionally, U.S. Pat. No. 4,731,073 discloses a prosthesis which is constructed from various zones of both solid and porous generally polyether-polyurethane materials. However, the artificial arterial vessel prepared according to the process disclosed in the U.S. Patent is surely larger than that of the conventional small vessel prosthesis. Furthermore, the U.S. Patent discloses the use of a single solid zone only when it is enclosed by non-interfacing porous zones. The compilation of zones disclosed in the U.S. Patent necessarily restricts the potential diameter size of an artificial prostheses, which in turn restricts the degree by which the prosthesis can be matched with its host. Additionally, the interface surfaces are not specifically designed to perform as blood and tissue interfacing surfaces, as in the present invention.

It is therefore an object of the present invention to provide a vascular prosthesis which is readily manufacturable to any length and compliance desired.

It is another object of the present invention to provide a vascular prosthesis which is manufactured from a material which remains stable in vivo.

It is yet another object of the present invention to provide a vascular prosthesis which can be compliance matched to the host vessel.

It is yet another object of the present invention to provide a vascular prosthesis which is designed to retain its compliance following healing of the perigraft tissues.

It is a further object of the present invention to provide a vascular prosthesis with excellent suture retention.

It is still a further object of the present invention to provide a vascular prosthesis available for small vessel prostheses.

It is still a further object of the present invention to provide a vascular prosthesis which will remain uniformly compliant subsequent to healing.

SUMMARY OF THE INVENTION

The present invention has several distinct advantages compared to alternative designs. In one embodiment, the prosthesis is composed entirely of silicone rubber, a material with the in vivo stability required for a permanent implant. Its characteristics, including its interior, medial and exterior can be independently varied to obtain the best configuration. It is readily manufacturable, and has handling characteristics likely to appeal to the vascular surgeon.

Because the prosthesis is easily adjustable to be implanted into the host by varying the solid unitary medial layer thickness, it is possible to have prostheses of different thicknesses and elasticities available to suit the needs of individual patients for commercially available prostheses.

The invention contains a circulatory system non-pyrogenic vascular prosthesis. In one embodiment, the vascular prosthesis comprises a small vessel prosthesis. Each prosthesis comprises a multilaminar tubular member. The multilaminar tubular member comprises an interior stratum, a medial stratum and an exterior stratum. In the construction of the tubular member, the medial stratum comprises of a unitary solid layer, while the interior and exterior strata comprise at least one layer per stratum.

The interior stratum forms a pseudoneointima-facilitating lumen surface which comes into direct proximity to the blood flowing through the host. Immediately external to this stratum is the unitary medial stratum. The unitary medial stratum forms an exclusionary boundary between the interior and exterior strata and is the sole layer which lies between the interior and exterior strata. Immediately external to the medial stratum is the exterior stratum. The exterior stratum forms a stabilization promoter surface which is designed for obtaining tissue attachment with the host.

One of the keys to this invention lies in the independently anatomically compatible entities. The interior, medial and exterior strata comprise the independently anatomically compatible entities which may be independently varied. The interior and exterior strata may be independently varied with a view to the degree of blood or tissue interaction, respectively. The thickness of the medial stratum may be independently varied for fostering post operative healing and positional stability.

The method of constructing the above-mentioned vascular prosthesis according to this invention is characterized in that the medial stratum is formed, on which an exterior stratum is applied. The medial stratum is then everted and the interior stratum is applied to the outer surface of the medial stratum, in the same manner as the exterior stratum was previously applied. The medial stratum is then reverted.

BRIEF DESCRIPTION OF THE DRAWINGS

The invention will be more fully understood by reading the following description in conjunction with the figures described below in which like reference numbers refer to like members.

DETAILED DESCRIPTION OF THE PREFERRED EMBODIMENTS

Figure 1:
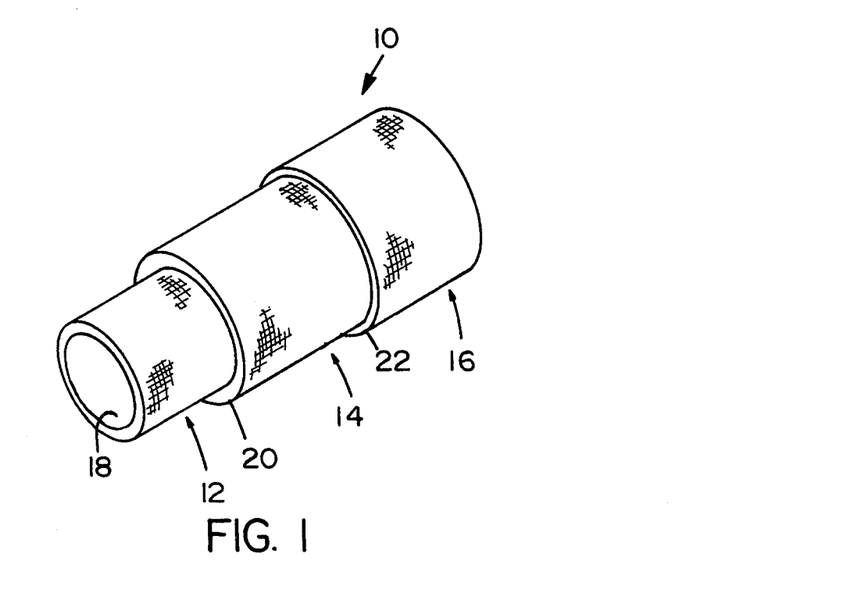
FIG. 1 is a plan view of the vascular prosthesis of the present invention.

Referring more particularly to the drawings, FIG. 1 shows a non-pyrogenic vascular prosthesis for use in channeling a biofluid. Non-pyrogenic is a term which refers to a substance which will not cause a fever. Biofluid is an expansive term which refers to physiological fluids including, but not limited to, blood, lymph, cerebrospinal fluid, lacrimal fluid, bile, urine, semen, and ascites fluid. Channeling, as effected by the non-pyrogenic vascular prosthesis of this invention, refers to the establishment of a means by which biofluid is enabled to flow or move through the prosthesis as located within a subject. In practice this will arise when the prosthesis is located with one end in fluid connection with a source of higher hydrostatic pressure and the other end in fluid connection with a source of lower hydrostatic pressure. Such a situation would occur in blood flowing upstream to downstream.

Vascular is a term which will refer not only to all blood vessels within the body, but in addition, it will refer to all biofluids as above-described. The vascular prosthesis shown in FIG. 1 will be generally referred to by reference number 10.

In one embodiment of the present invention the vascular prosthesis is constructed from silicone rubber. One variation of this silicone rubber may refer to a medical grade silicone rubber formulation which usually comprises dimethyl and methylvinyl siloxane copolymers and optionally reinforcing silica. One advantage of using silicone rubber for the prosthesis is that it does not degrade in vivo, as is the case with many polyurethanes.

This material is supplied in two component solid form. The components must be blended using a two roll mill to thoroughly mix the constituents, preferably soon before actual use. The blended material can the be thermally cured via addition-cure chemistry, the advantage of which are that this system produces no peroxide residues or volatile by-products. When cured, this is a highly cross-linked material, and as a result, it has physical characteristics that are especially useful for the invention.

In one embodiment, the tensile strength of the silicone rubber is in the range of 1300 psi with a 1,000% elongation at failure. It has excellent tear resistance (190 ppi), and as a result the material is readily suturable and may be cut without fear of fault propagation. The prosthesis may be safely cut to length at the time of implantation, is readily sutured, may be cross-clamped with impunity, and is also autoclavable for sterilization.

The vascular prosthesis 10 comprises a non-pyrogenic multilaminar tubular member. The multilaminar tubular member is a term used in relation to the present invention to means the construction of a vascular prosthesis from at least three strata components. In one embodiment, the multilaminar tubular member is used in vascular reconstruction surgery. Coronary revascularizaiton is potentially the most significant market for a small vessel prosthesis. Coronary revascularization in the unique tissue environment of the thorax is also a potential use for the present invention.

Figure 2:
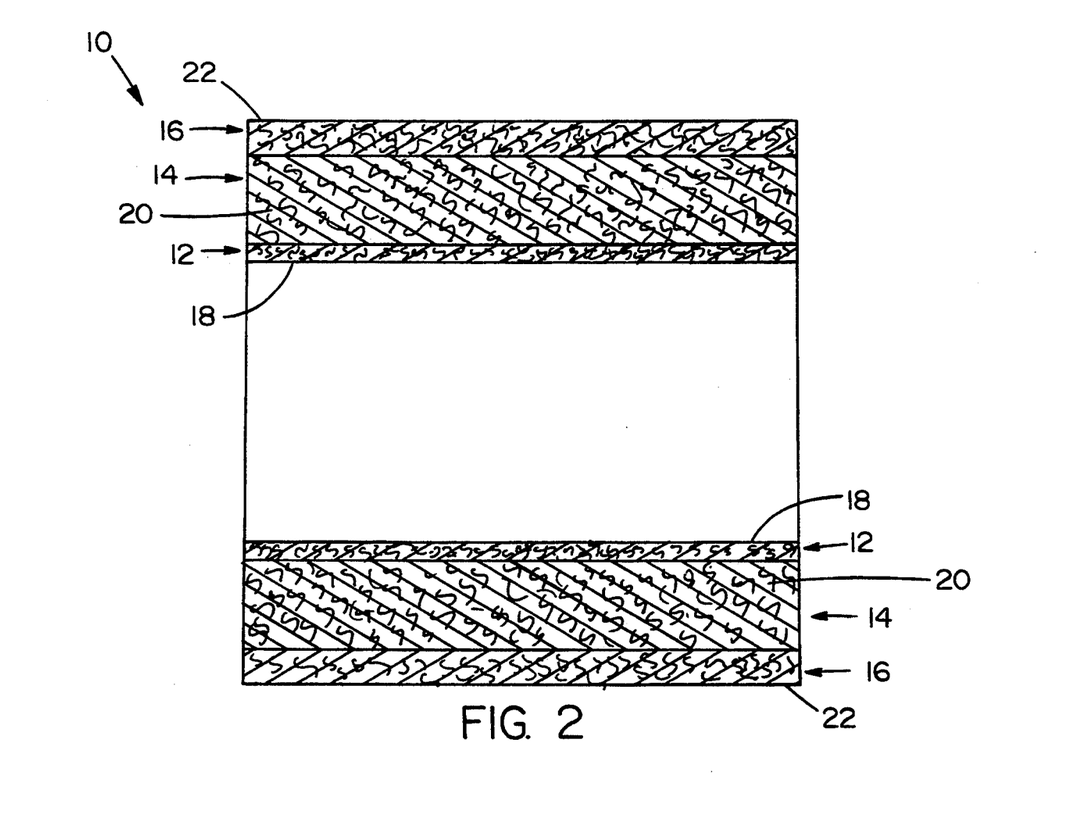
FIG. 2 is a cross-sectional view of the vascular prosthesis of the present invention.

As shown in FIGS. 1 and 2, the multilaminar tubular member comprises an interior stratum 12, a medial stratum 14 and an exterior stratum 16. The interior stratum 12 is defined as an inner surface of the multilaminar tubular member which bears a pseudoneointima (PNI)-facilitating lumen surface 18.

The PNI-facilitating lumen surface is a term which refers to the surface with which blood comes into direct proximity and thereafter behaves as a blood-compatible intima. In one embodiment, the PNI-facilitating lumen surface is a textured porous surface which interacts with blood flowing over its surface to generate a PNI.

Blood-compatible intima, is the term used to refer generally to the characterization of a surface phenomenon which effectively masks a synthetic material from host response usually associated with a foreign material within the circulation. The term host refers to the vessel or artery in which the prosthesis is implanted. The term host response, as used in the explanation of the blood-compatible intima, refers to the biological reaction which develops within the host when foreign material is implanted.

In the example of a textured PNI-facilitating lumen surface exposed to blood, blood-compatible intima development is initiated by protein adsorbtion on the surface rapidly followed by platelet adhesion, fibrin deposition, and the entrapment of other formed elements from blood. These are usually presented as elements flowing over the PNI-facilitating lumen surface. While not being bound by any particular theory it is currently understood that this early fibrin/platelet coagulum then undergoes organization to produce the PNI and renders the surface blood compatible.

Furthermore, while not being bound by any particular theory it is currently understood that the occurrence of the PNI at the textured surface is thought to be primarily mechanical rather than adhesive in nature, since the material of the textured surface is itself chemically inert and does not offer covalent bonding sites. Because the textured surface is located on a solid substrate, the PNI also is isolated from ingrowth by external tissues or contact with tissue thromboplastins released from surgically sectioned tissue other than at its end points where it is connected to the vascular system.

The PNI-facilitating lumen surface is also suitable as a substrate for endothelial cell seeding or similar surface modifications to aid in the formation of its pseudoneointima.

In one embodiment, the thickness of the stratum for the blood contacting surface is approximately $300\mu$. The dimensions of the surface porosity can range form $90\mu$ to $170\mu$. This thickness and surface morphology is adjustable during processing to permit the surface to be used directly as a blood contacting surface or for use as a matrix for a cell seeded surface.

As shown in FIGS. 1 and 2, the medial stratum 14, which is an integral part of the multilaminar tubular member, comprises a unitary layer which yields an exclusionary boundary 20 between an interior stratum 12 and exterior stratum 16.

The exclusionary boundary 20 is a term used to refer to the solid non-porous non-communicative surface which solely acts to encapsulate the PNI-facilitating lumen surface 18 and prohibit communication between the PNI-facilitating lumen surface 18 and a stabilization promoter surface 22.

While not being bound by any particular theory, it is currently understood that the mechanical properties of the prosthesis are determined principally by the thickness and composition of this non-communicative substrate. The textured interior and exterior surfaces, made in accordance with one embodiment, do not significantly change the measured mechanical properties of the finished prosthesis compared to the uncoated solid exclusionary boundary substrate. The use of a unitary solid substrate, as shown in FIGS. 1 and 2, is thus particularly important to facilitate the manufacturing ability to independently vary the mechanical properties of this substrate while maintaining a desired blood compatible intima in the PNI-facilitating lumen surface 18, in order to precipitate compatibility with its host.

One advantage of this architecture is that it now becomes possible to make a vascular prosthesis of a specific compliance. The term compliance refers to the degree of elasticity of the radius of the prosthesis, or radial elasticity, which is required to enable the prosthesis to expand from internal pressure. The radial elasticity of a prosthesis can be produced by using an appropriately selected elastomer for the exclusionary boundary in order to prevent customary host response associated with a rigid foreign material within the circulation. The vascular prosthesis may thus be matched to the host, including a host with abnormal compliance properties, by varying the compliance of the exclusionary boundary 20. This is thought to minimize the incidence of intimal hyperplasia of the arterial tissue sutured to the prosthesis, a major cause of failure of existing small vessel prosthesis. Clinical experiments have indicated that the compliance required of a vascular prosthesis is relatively small. For example, human femoral arteries from patients have been measured to have a compliance of $9.1 \pm 1.6\%$ radial change/mmHg X $10^{-2}$. The total diametrical change associated with a pulse pressure difference of 40 mmHg in a vessel of 5–7 mm internal diameter is thus on the order of only 200–$300\mu$. This corresponds to a mechanical strain of less than 5%.

It has long been postulated that the response at the anastomoses of a synthetic prosthesis which has not been matched to the natural tissue of the host is an important factor in the poor performance of available small vascular prostheses. A vascular prosthesis which is designed to correspond to the dimensions and elasticity of the host is thought to lessen the potential for intimal hyperplasia at the anastomoses, an almost universal finding with conventional synthetic vascular prostheses. Intimal hyperplasia is especially compromising to the function of a small caliber prosthesis, since it narrows the already limited available lumen and more significantly alters flow patterns compared to a large caliber vessel.

In addition, the vascular prosthesis does not require any preclotting before implantation, as there is no bleeding through the exclusionary boundary.

In one embodiment, using silicone rubber elastomer of the type described, the thickness of the exclusionary boundary is in the range of 0.5–0.75 mm. This single solid layer results in a prosthesis with good flexibility and bendability, which is readily manufacturable with a desired radial compliance. It is thus possible for the surgeon to specify a compliance for the graft above or below the physiologic range, were that shown to be desirable. For example, a patient with significant atherosclerosis may then receive a compliance matched prosthesis where the prosthesis was of reduced compliance compared to a normal physiologic value. To achieve this reduced compliance, the prosthesis is manufactured with an exclusionary boundary of increased thickness.

As shown in FIGS. 1 and 2, the exterior stratum 16, which is an integral part of the multilaminar tubular member, comprises an outer surface of the multilaminar tubular member which bears a stabilization promoter surface 22.

The stabilization promoter surface 22 comprises an outer surface of the vascular prosthesis. The stabilization promoter surface 22 encapsulates the exclusionary boundary 20 and is designed specifically with a surface topography optimized for obtaining tissue attachment, and particularly soft tissue attachment, to the structures exterior of the implant to stabilize the location of the vascular prosthesis 10. The stabilization promoter surface 22 also provides a diminished host response usually associated with a foreign material within the circulation. Such diminished host response is useful in fostering post operative healing and positional stability.

Figure 4:
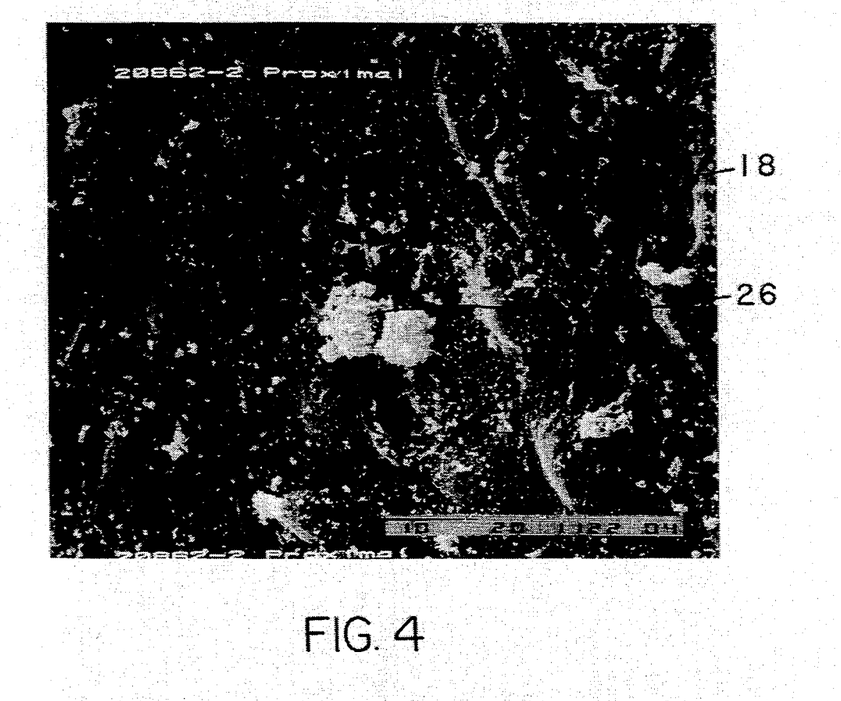
FIG. 4 is a cross-sectional view taken with a scanning electron micrograph of the interior surface of a vascular prosthesis of a canine after 8 weeks from implantation.

In one embodiment, the stabilization promoter surface is textured and porous, similar to the endothelial cells 18 which constitute the PNI-facilitating lumen surface in FIG. 4. In another embodiment, the porous surface appropriate for the blood compatible intima at the PNI-facilitating lumen surface may be different from that which is best for the tissue at the stabilization promoter surface 22. While not being bound by any particular theory it is currently understood that the PNI thickness in the blood compatible intima is at least in part directly related to surface pore size. While it is advantageous to reduce PNI thickness by using smaller pore sizes, there is a minimum pore size for surfaces of this type beyond which PNI attachment to the surface is compromised and the PNI will be unstable. In contrast, there is an inverse relationship between pore size and tissue thickness where the tissue attaches in the stabilization promoter surface. At this site, a large pore size with comparatively open architecture produces a minimum tissue thickness with the best adhesion.

In one embodiment, the surface porosity of the stabilization promotor surface is in the range of 170µ to 220µ with a thickness of approximately 400µ.

One of the key aspects of this invention is the anatomically compatible entity status of each stratum. The term anatomically compatible entity refers to the individual strata which comprise this vascular prosthesis, minimally these include the interior, medial and exterior strata. More specifically, it is the ability of each of the strata to be independently modified. The interior and exterior strata may be independently modified with a view to the degree of blood or tissue interaction, respectively. The thickness of the solid unitary medial stratum may be modified for the purpose of fostering post operative healing and positional stability. In a particular embodiment, the three layers are united in a vascular prosthesis of the present invention.

Figure 3:
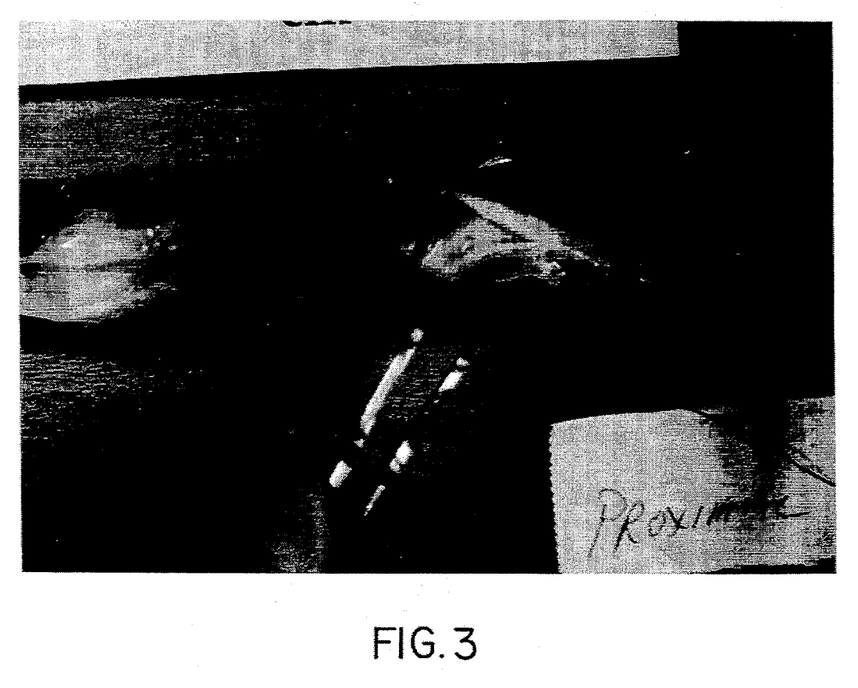
FIG. 3 is a cross-sectional view of the suture line of an explanted vascular prosthesis of a canine after 8 weeks from implantation.

The histologic findings of explanted devices from tests which were conducted on canines were most instructive. PNI morphology on the textured interior surface of the prosthesis showed a thin, adherent PNI which was undergoing organization at a rate typically seen in canine studies. FIG. 3 shows a cross sectional view of the prosthesis which was explanted for inspection. The proximal anastomoses revealed the healed suture line 24 within the prosthesis and the absence of excessive intimal overgrowth from the arterial tissue.

FIG. 4 shows a scanning electron micrograph of the interior textured surface of a healed graft from a canine animal after 8 weeks. The surface is covered with a continuous layer of endothelial cells 18 at the blood interface, which which make up the luminal surface of the PNI, effectively masking the synthetic material of the prosthesis from blood contact and resulting in a highly blood compatible, non-thrombogenic surface. Reference number 26 refers to a white blood cell which is sitting on the surface of the PNI. The bulk of the PNI is acellular, consisting largely of fibrin with some collagen and and occasional fibroblasts. The PNI in contact with the textured surface shows the irregular contour of the textured surface that had supported it. In general, the PNI in the central regions of the prostheses was quite thin, typically on the order of 100–200µ in total thickness. At the anastomoses, the PNI is thicker, since the PNI-facilitating lumen surface there becomes covered with cells from the adjacent arterial tissue. The PNI in that region is thus more highly organized, containing a confluent layer of cells at the blood interface, numerous fibroblasts, and collagen fibers oriented along the axis of the vessel.

Figure 5:
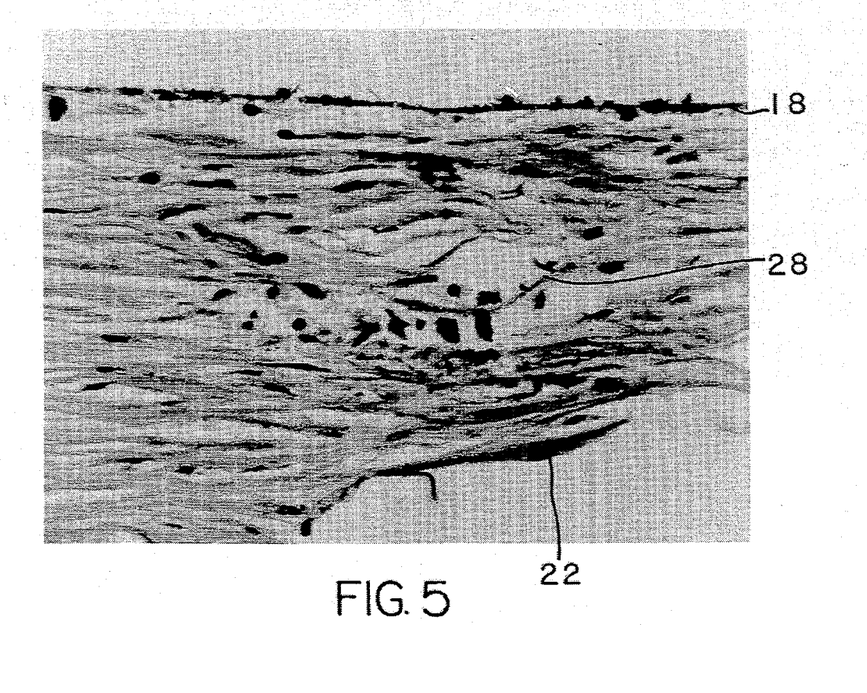
FIG. 5 is a cross-sectional view taken with a photomicrograph at the junction of the aortic tissue and prosthesis of a canine.

FIG. 5 shows a cross sectional view of the prosthesis taken by a photomicrograph at the proximal anastomoses 28 at the junction of the aortic tissue and prosthesis. It is generally understood that healing at the anastomoses proceeds significantly more rapidly here than in the central region of the prosthesis, as it almost assuredly originates from the adjacent arterial tissue.

Figure 6:
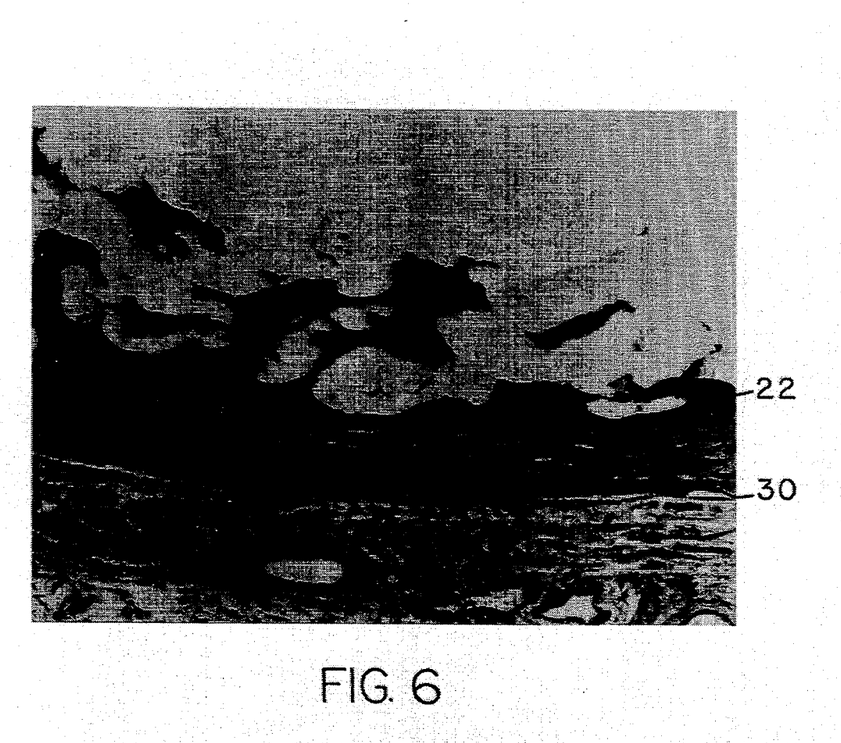
FIG. 6 shows a cross sectional view taken with a photomicrograph of the prosthesis of the same canine as shown in FIG. 4.

FIG. 6 shows a cross sectional view of the prosthesis taken by a photomicrograph of the same animal as shown in FIG. 5. In this view, the stabilization promoter surface 22 is facing the prosthesis is at the bottom. The ingrowth of the tissue capsule 30 into the more open textured stabilization promoter surface of the prosthesis is evident. There appear to be inflammatory cells in contact with the stabilization promoter surface of the prosthesis, but the tissue capsule is thin. The tissue capsule consisted of a translucent covering through which the stabilization promotor surface was readily seen. This prosthesis and others resembling it remained compatible with its host throughout the procedure.

The animal studies demonstrated, among other things, that the prosthesis exhibits high patency rates in animal testing. Additionally, the studies show that the stabilization promotor surface is effective in obtaining a thin, stable tissue capsule around the implants so that the compliance of the graft is retained.

Figure 7:
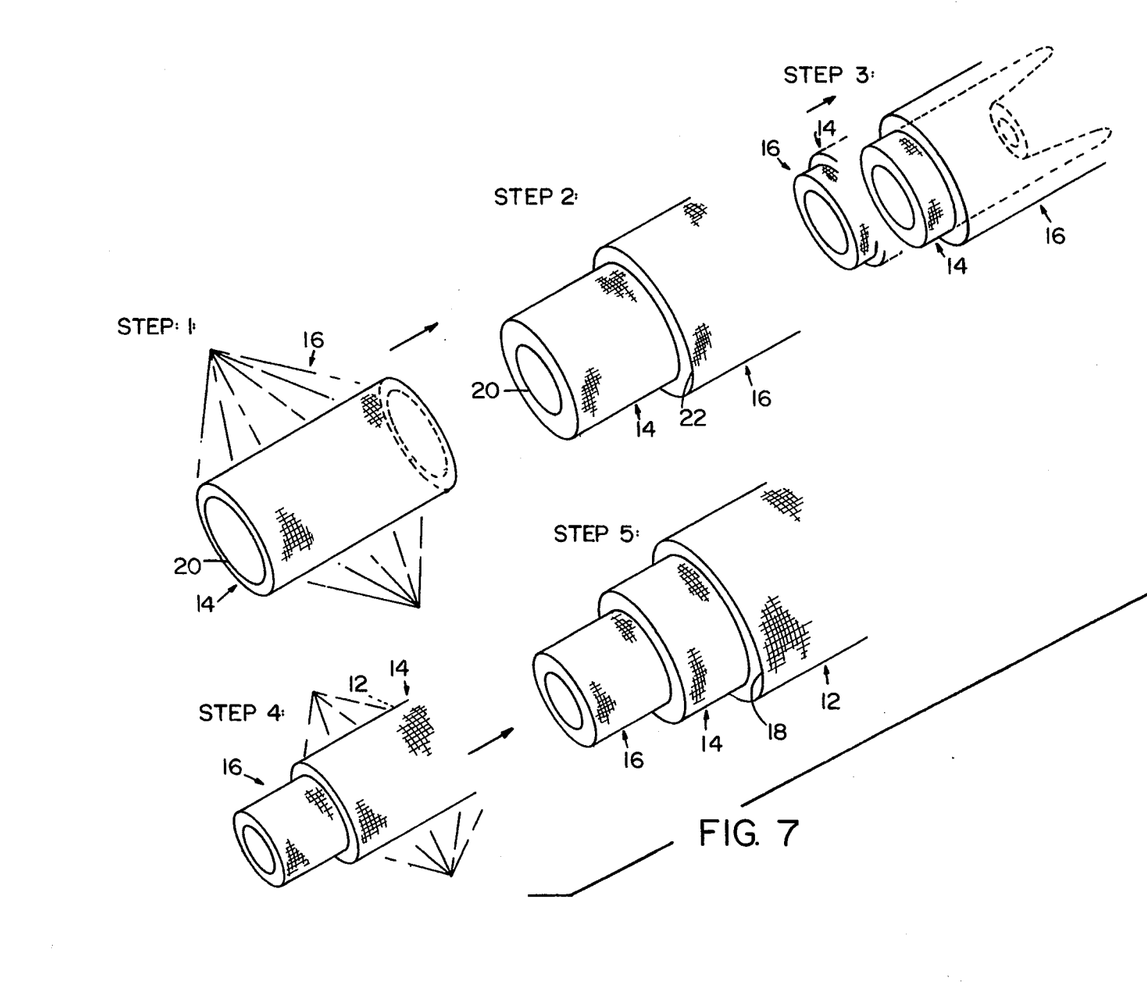
FIG. 7 is a plan view of the method of construction of the vascular prosthesis of the present invention.

FIG. 7 shows generally a schematic embodiment of the method of manufacturing the vascular prosthesis according to the present invention. The method shown comprises the first step of preparing the solid unitary medial stratum 14, which forms the exclusionary boundary 20. The thickness and elasticity of the medial strata must first be evaluated in comparison with the host. In one embodiment, the medial stratum may be made by either of two embodiments, the process of compression molding or solution casting. The could be tapered in diameter along its length, and the thickness can be adjusted to comply with any desired degree of radial compliance.

The medial stratum 14 once demolded is externally coated with a surface. This surface is the exterior stratum 16, which forms the stabilization promoter surface 22. In one embodiment as shown in FIG. 7, the exterior stratum 16 is applied by spraying the solvent dispersed but uncured elastomer directly on the medial stratum surface 14, as shown in Step 1 of FIG. 7. The coating which comprises the exterior stratum, as shown in Step 2 of FIG. 7, may, in one embodiment, be cured in a circulating oven at a temperature of 170° C.

The first coating means is then followed by a second coating means. The media stratum 14 is first everted as in Step 3 of FIG. 7, and the same means used for preparation of the exterior stratum 16 is used for preparation of the interior stratum 12, as seen in Step 4 of FIG. 7, which forms the PNI-facilitating lumen surface 18, as seen in Step 5 of FIG. 7. In one embodiment, the applied coating on the interior stratum is thinner than that of the exterior stratum.

In another embodiment, both the interior stratum and the exterior stratum result in a textured porous surface. In another embodiment of the invention, the interior stratum is both thinner than the exterior stratum and has a smaller pore size than the exterior stratum.

Further, the multilaminar tubular member is then reverted (not shown), by repeating Step 3 of FIG. 7, and any residual solvent is removed through a water extraction process. In one embodiment, the completed vascular prosthesis is autoclaved for sterilization prior to in vivo use.

Figure 8:
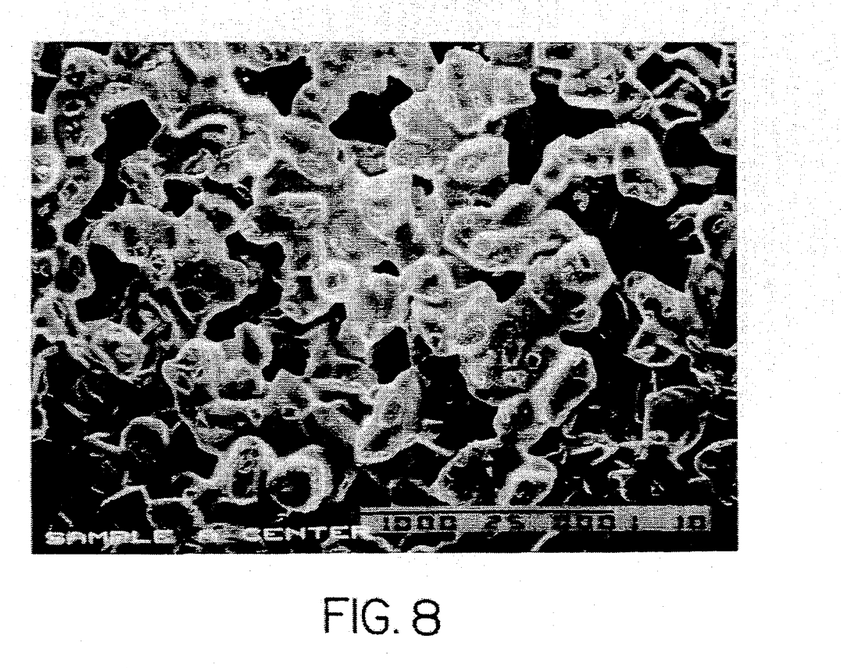
FIG. 8 is a low power scanning electron micrograph view of the textured silicon rubber surface prepared in accordance with the method shown in FIG. 6

FIG. 8 is a low power scanning electron micrograph view of the textured silicone rubber surface prepared in accordance with this method.

The embodiments which have been described herein are but some of the several which utilize this invention and are set forth here by way of the illustration but not of limitation. It is apparent that many other embodiments which will be readily apparent that are skilled in the art may be made without departing materially from the spirit and scope of this invention.

What is claimed is:

1. A circulatory system non-pyrogenic vascular prosthesis having variable radial elasticity, which prosthesis comprises:

a multilaminar tubular member comprising an interior stratum, a unitary medial stratum having an internal and external diameter, and an exterior stratum wherein said interior stratum bears a pseudoneointima-facilitating lumen surface;

said exterior stratum bears a stabilization promoter surface;

said interior and exterior strata being separated solely by said unitary medial stratum;

said unitary medial stratum being a solid, non-porous, non-communicative exclusionary boundary which prohibits communication between the pseudoneointima-facilitating lumen surface and the stabilization promoter surface and which has a thickness that can vary such that said internal diameter varies while said external diameter remains constant;

said variable radial elasticity varying inversely with the thickness of said unitary medial stratum.

2. A circulatory system vascular prosthesis according to claim 1 wherein the interior stratum comprises textured porous material.

3. A circulatory system vascular prosthesis according to claim 1 wherein the exterior stratum comprises textured porous material.

4. A circulatory system vascular prosthesis according to claim 1 wherein the interior stratum has thinner walls and smaller pore size than the exterior stratum.

5. A circulatory system vascular prosthesis according to claim 1 wherein the interior, medial and exterior strata are fabricated from a single, biostable material entirely without the use of adhesives.

6. A circulatory system vascular prosthesis according to claim 1 wherein the interior stratum has a thickness of approximately 300μ and a surface porosity in the range of 90μ to 170μ and the exterior stratum has a thickness of approximately 400μ and a surface porosity in the range of 170μ to 220μ.

7. A circulatory system vascular prosthesis according to claim 1 wherein the interior, medial and exterior strata are composed of silicone rubber.

8. A circulatory system vascular prosthesis according to claim 7 wherein the unitary medial stratum has a thickness in the range of 0.5 mm to 0.75 mm.

* * * * *

UNITED STATES PATENT AND TRADEMARK OFFICE
CERTIFICATE OF CORRECTION

PATENT NO. : 5,354,329
DATED : Oct. 11, 1994
INVENTOR(S) : Whalen, R.L

It is certified that error appears in the above-indentified patent and that said Letters Patent is hereby corrected as shown below:

Column 5; line 15: "means" should read "mean"
Column 6; line 5: "form" should read "from"
Column 9; line 12: insert "medial stratum" after "the"

Signed and Sealed this

Eleventh Day of April, 1995

Attest:

BRUCE LEHMAN

Attesting Officer      Commissioner of Patents and Trademarks